United States Patent
Li et al.

(10) Patent No.: US 11,819,561 B2
(45) Date of Patent: Nov. 21, 2023

(54) ORAL CARE COMPOSITIONS

(71) Applicant: Colgate-Palmolive Company, New York, NY (US)

(72) Inventors: Ningwei Li, Highland Park, NJ (US); Hongwei Shen, Holmdel, NJ (US); Saide Tang, Princeton, NJ (US); Betty Won, Princeton Junction, NJ (US); Viktor Dubovoy, Cresskill, NJ (US); Long Pan, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 21 days.

(21) Appl. No.: 17/359,026

(22) Filed: Jun. 25, 2021

(65) Prior Publication Data

US 2021/0401705 A1    Dec. 30, 2021

Related U.S. Application Data

(60) Provisional application No. 63/044,522, filed on Jun. 26, 2020.

(51) Int. Cl.
| | |
|---|---|
| A61K 8/43 | (2006.01) |
| A61K 8/24 | (2006.01) |
| A61Q 11/00 | (2006.01) |

(52) U.S. Cl.
CPC .......... *A61K 8/43* (2013.01); *A61K 8/24* (2013.01); *A61Q 11/00* (2013.01); *A61K 2800/28* (2013.01); *A61K 2800/48* (2013.01); *A61K 2800/524* (2013.01); *A61K 2800/5422* (2013.01); *A61K 2800/5426* (2013.01); *A61K 2800/5428* (2013.01); *A61K 2800/74* (2013.01)

(58) Field of Classification Search
CPC . A61Q 11/00; A61K 8/43; A61K 8/24; A61K 2800/28; A61K 2800/48; A61K 2800/524; A61K 2800/5422; A61K 2800/5426; A61K 2800/5428; A61K 2800/74; A61K 8/442; A61K 8/466; A61K 8/4926; A61K 8/604

See application file for complete search history.

(56) References Cited

U.S. PATENT DOCUMENTS

| | | | |
|---|---|---|---|
| 5,695,745 A | 12/1997 | Barton et al. | |
| 6,190,644 B1 * | 2/2001 | McClanahan | A61K 8/19 424/49 |
| 8,628,755 B2 * | 1/2014 | Prencipe | A61K 8/33 424/49 |
| 9,005,586 B2 * | 4/2015 | Prencipe | A61K 8/33 424/49 |
| 9,561,160 B2 * | 2/2017 | Rege | A61Q 11/00 |
| 9,801,795 B2 * | 10/2017 | Nesta | A61K 8/60 |
| 9,877,903 B2 * | 1/2018 | Prencipe | A61K 8/4953 |
| 10,238,896 B2 | 3/2019 | Myers et al. | |
| 2014/0335029 A1 * | 11/2014 | Rudolph | A61Q 15/00 560/126 |
| 2016/0376263 A1 * | 12/2016 | Patron | C07D 413/14 514/784 |
| 2017/0049671 A1 * | 2/2017 | Prencipe | A61K 8/731 |
| 2017/0348213 A1 | 12/2017 | Xu et al. | |
| 2018/0043190 A1 | 2/2018 | Myers et al. | |

FOREIGN PATENT DOCUMENTS

| | | | |
|---|---|---|---|
| DE | 102006060947 | 9/2008 | |
| JP | H06-239723 | 8/1994 | |
| RU | 2527692 | 8/1996 | |
| WO | WO-9412150 A1 * | 6/1994 | ........... A61K 38/164 |
| WO | 2007/011552 | 1/2007 | |

OTHER PUBLICATIONS

Barkvoll, et al., "Interaction between chlorhexidine digluconate and sodium lauryl sulfate in vivo," J Clin Periodontol, 16 (9):593-5 (1989).

Addy, M., "Chlorhexidine compared with other locally delivered antimicrobials," Journal of Clinical Periodontology, 13 (10):957-964 (1986).

International Search Report issued in International Application PCT/US2021/039167 dated Nov. 5, 2021.

McDonnell, et al., "Antiseptics and Disinfectants: Activity, Action, and Resistance," Clinical Microbiology Reviews 12 (1):147-179 (1999).

Roy et al., "Amino Acid Based Cationic Surfactants in Aqueous Solution:? Physicochemical Study and Application of Supramolecular Chirality in Ketone Reduction," Langmuir, 21(23):10398-10404 (2005).

* cited by examiner

*Primary Examiner* — Isaac Shomer
*Assistant Examiner* — Amanda Michelle Petritsch

(57) ABSTRACT

This application provides, among other things, novel aqueous oral care compositions useful for combining and delivering poorly compatible ingredients, in particular, chlorhexidine and polyphosphate salts, by formulating the composition with a surfactant.

19 Claims, No Drawings

ORAL CARE COMPOSITIONS

CROSS-REFERENCE TO RELATED APPLICATIONS

This application is a United States application filed under 35 U.S.C. § 111(a) claiming priority to and the benefit of U.S. Provisional Application No. 63/044,522, filed on Jun. 26, 2020, the contents of which are hereby incorporated by reference in its entirety.

BACKGROUND

This application relates, inter alia, to novel aqueous oral care compositions useful for combining and delivering poorly compatible ingredients, in particular, chlorhexidine and polyphosphate salts, by formulating the composition with a surfactant.

Biofilms form when bacteria adhere to surfaces in some form of watery environment and begin to excrete a slimy, glue-like substance that can stick to all kinds of materials—metals, plastics, soil particles, medical implant materials, biological tissues. Dental plaque is a biofilm that adheres to tooth and other oral surfaces, particularly at the gingival margin, and is implicated in the occurrence of gingivitis, periodontitis, caries and other forms of periodontal disease. Dental plaque is cohesive and highly resistant to removal from teeth and/or oral surfaces. Bacteria associated with dental plaque convert sugar to glucans, which are insoluble polysaccharides that provide plaque with its cohesive properties. Anaerobic bacteria in plaque metabolize sugar to produce acids which dissolve tooth minerals, damaging the enamel and eventually forming dental caries. Saliva can buffer acids produced by bacteria and promote remineralization of the enamel, but extensive plaque can block the saliva from contact with the enamel. Redeposition of minerals in the biofilm forms a hard deposit on the tooth called calculus (or tartar), which becomes a local irritant for the gums, causing gingivitis.

Various antibacterial agents can retard the growth of bacteria and thus reduce the formation of biofilm on oral surfaces. An important and highly effective antibacterial agent for this purpose is the cationic bisguanide agent chlorhexidine.

A tooth is comprised of an inner dentin layer and an outer hard enamel layer that is the protective layer of the tooth. The enamel layer of a tooth is naturally opaque, and white or a slightly off-white color. The enamel layer is composed of hydroxyapatite mineral crystals that create a somewhat porous surface. These hydroxyapatite crystals form microscopic hexagonal rods or prisms that make up the enamel surface. As a result, the surface of the enamel presents microscopic spaces or pores between the prisms. Without limiting the mechanism, function, or utility of the present disclosure, it is believed that this porous nature of the enamel is where discoloring substances permeate the enamel and discolor the teeth. Everyday activities such as smoking or other oral use of tobacco products, and eating, chewing or drinking certain foods and beverages (particularly coffee, tea, cola drinks, and red wine), can cause undesirable staining of the surfaces of teeth. Staining can also result from microbial activity, including that associated with dental plaque.

Since the compounds that stain the teeth are typically anionic materials, cationic antibacterial agents such as chlorhexidine can cause or enhance staining by facilitating the deposit of chromogens or by forming salts with minerals.

One approach to reducing staining and erosion, as well as reducing biofilm formation, is the use of a dentifrice, such as a mouthwash, containing mineral agents useful in stain removal. Polyphosphate salts, for example, exhibit significant stain fighting ability, and when used in oral care products, they deposit onto and protect the tooth surface, as well as complexing with free calcium, thereby starving bacteria and reducing calculus deposition. However, when phosphates are combined with cationic antibacterial agents, particularly in high water formulations where the two can readily interact in solution, the phosphates and the cationic antibacterial agents can complex to form insoluble precipitates, thereby inactivating both components.

Thus, while polyphosphates, such as sodium tripolyphosphate, can prevent the tooth staining caused or induced by chlorhexidine, the adverse interaction between these agents must be prevented to enable the compositions to have maximum oral efficacy.

Anionic surfactants such as sodium lauryl sulfate have been suggested to help stabilize chlorhexidine and polyphosphate salts in aqueous solution, but such surfactants can be irritating to soft tissues, and their use has come under limiting regulation. In addition, it has been found that sodium lauryl sulfate-stabilized chlorhexidine/polyphosphate mouthwashes are susceptible to issues of haziness, possibly due to the formation of excessively large micelles.

There is thus a need for novel oral compositions and methods that inhibit staining and biofilm formation, and in particular that can provide both the anti-staining and anti-calculus benefits of phosphates and also the anti-bacterial and anti-biofilm benefits of a chlorhexidine.

BRIEF SUMMARY

Bisguanide antimicrobial agents such as chlorhexidine will generally complex with anionic polyphosphate salts, given their high charge density and entropically driven precipitation reaction. Chlorhexidine will also react with anionic surfactants such as sodium lauryl sulfate and thus is often considered incompatible with sodium lauryl sulfate. See, e.g., Barkvoll, et al., "Interaction between chlorhexidine digluconate and sodium lauryl sulfate in vivo," J Clin Periodontol. (1989)16(9):593-5.

The inventors have unexpectedly found that addition of a stabilizing amount of a surfactant, e.g., a zwitterionic, cationic, nonionic, or certain anionic surfactants, to a mouthwash composition comprising chlorhexidine (e.g., chlorhexidine digluconate) can result in the formation of stabilized micelles. Without being bound by theory, it is believed that these micelles allow the chlorhexidine to remain compartmentalized from the polyphosphate agents (e.g., sodium tripolyphosphate) in the mouthwash solution. Thus, adverse interactions between these components are inhibited and effective delivery of these agents to the teeth is enhanced.

The present disclosure thus provides an aqueous oral care composition comprising:
  (i) an effective amount of an orally acceptable guanide antibacterial agent selected from a bisguanide (e.g., chlorhexidine, such as chlorhexidine digluconate), or a poly(hexamethylene biguanide) (e.g., polihexanide);
  (ii) a short chain linear polyphosphate salt (e.g., potassium or sodium pyrophosphate or tripolyphosphate); and (iii) a stabilizing amount of a zwitterionic, cationic, or nonionic surfactant, or a fatty acyl amide or fatty acyl ester carboxylate or sulfonate surfactant, or a combination thereof.

The present disclosure further provides methods of inhibiting dental erosion, staining, and/or biofilm formation comprising administering to the oral cavity a composition as described herein.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

As is usual in the art, the compositions described herein are sometimes described in terms of their ingredients, notwithstanding that the ingredients may disassociate, associate or react in the formulation. Ions, for example, are commonly provided to a formulation in the form of a salt, which may dissolve and disassociate in aqueous solution. It is understood that the invention encompasses both the mixture of described ingredients and the product thus obtained.

In a first embodiment, the disclosure provides an oral care composition (Composition 1) comprising:
 (i) an effective amount of an orally acceptable guanide antibacterial agent selected from a bisguanide (e.g., chlorhexidine, such as chlorhexidine digluconate), or poly(hexamethylene biguanide) (e.g., polihexanide);
 (ii) a short chain linear polyphosphate salt (e.g., potassium or sodium pyrophosphate or tripolyphosphate); and
 (iii) a stabilizing amount of a zwitterionic, cationic, or nonionic surfactant, or a fatty acyl amide or fatty acyl ester carboxylate or sulfonate surfactant, or a combination thereof.

For example, the disclosure provides embodiments of Composition 1 as follows:
1.1 Composition 1, wherein the biguanide is chlorhexidine.
1.2 Composition 1.1, wherein the chlorhexidine is in the form of chlorhexidine digluconate.
1.3 Any foregoing composition, wherein the composition comprises from 0.01 to 5 wt. % of the guanide agent, e.g., from 0.05 to 1 wt. %, or from 0.1 to 0.5 wt. % or from 0.1 to 0.3 wt. %, or about 0.2 wt. %, based on the total weight of the composition.
1.4 Any foregoing composition, wherein the short chain linear polyphosphate is a pyrophosphate or a tripolyphosphate.
1.5 Any foregoing composition, wherein the short chain linear polyphosphate salt is an alkali metal or alkaline earth metal salt, such as sodium, potassium, magnesium or calcium.
1.6 Any foregoing composition, wherein the short chain linear polyphosphate salt is selected from sodium tripolyphosphate, tetrasodium pyrophosphate, tetrapotassium pyrophosphate or combinations thereof.
1.7 Any foregoing composition, wherein the short chain polyphosphate salt is sodium tripolyphosphate.
1.8 Any foregoing composition, wherein the short chain polyphosphate salt is present in an amount of 0.01 wt. % to 5.0 wt. %, 0.1 wt. % to 5.0 wt. %, 0.1 wt. % to 3 wt. %, 0.5 wt. % to 2 wt. %, or 1.0 wt. % to 2 wt. %, or about 1.6 wt. %, based on the total weight of the composition.
1.9 Any foregoing composition, wherein the surfactant is a zwitterionic surfactant.
1.10 Composition 1.9, wherein the surfactant is a sultaine, hydroxysultaine or betaine surfactant.
1.11 Composition 1.10, wherein the surfactant is a surfactant selected from cocamidopropyl sultaine, cocamidopropyl hydroxysultaine, and cocamidopropyl betaine.
1.12 Composition 1.11, wherein the surfactant is cocamidopropyl betaine (CAPB).
1.13 Any foregoing composition, wherein the surfactant is a cationic surfactant.
1.14 Composition 1.13, wherein the surfactant is a quaternary ammonium surfactant, such as cetrimonium bromide, benzalkonium chloride, and benzethonium chloride.
1.15 Composition 1.13, wherein the surfactant is a quaternary pyridinium surfactant.
1.16 Composition 1.15, wherein the surfactant is cetylpyridinium chloride (CPC).
1.17 Composition 1.13, wherein the surfactant is an amino acid-based cationic surfactant, e.g., a quaternary $N^\alpha$—$(C_{12\text{-}30}$acyl)amino acid (e.g., $R^a$—$NH_2^+$—CH(R)—COOH, wherein $R^a$ is a $C_{12\text{-}30}$acyl chain and R is a natural or synthetic amino acid side group) or an $N^\alpha$-peralkylated-$N'$—$(C_{12\text{-}30}$alkyl)amino acid amide (e.g., $NMe_3^+$—CH(R)—$CONHR^a$ wherein $R^a$ is a $C_{12\text{-}20}$alkyl chain and R is a natural or synthetic amino acid side group), or an $N^\alpha$-acyl amino acid alkyl esters (e.g., $R^a$—$NH_2^+$—CH(R)—$COOR^b$, wherein $R^a$ is a $C_{12\text{-}30}$acyl chain, R is a natural or synthetic amino acid side group and $R^b$ is a $C_{1\text{-}6}$alkyl chain such as methyl or ethyl), and salts thereof.
1.18 Composition 1.17, wherein the amino-acid-based cationic surfactant is selected from (1-hexadecylcarbamoyl-ethyl)-trimethylammonium halide, (1-hexadecylcarbamoyl-2-phenyl-ethyl)-trimethylammonium halide, 1-hexadecylcarbamoyl-1,1-dimethyl-pyrrolidinium halide, and [2-(1H-indole-3-yl)-1-hexadecylcarbamoyl-ethyl)]-trimethylammonium halide, wherein said halide is optionally chloride, fluoride or bromide.
1.19 Composition 1.17, wherein the amino-acid-based cationic surfactant is selected from lauroyl arginine, ethyl lauroyl arginine ester hydrochloride, and disodium sebacoyl bis-lauramidolysine.
1.20 Any foregoing composition, wherein the surfactant is a nonionic surfactant.

1.21 Composition 1.20, wherein the surfactant is selected from fatty alcohol ethoxylates, alkylphenyl ethoxylates, fatty acid ethoxylates, ethoxylated amines or amides, polyoxyethylene/polyoxypropylene copolymers (poloxamers), glycerol fatty acid esters, sorbitol fatty acid esters, alkyl polyglucosides, and amine oxides.

1.22 Composition 1.21, wherein the surfactant is an alkyl polyglucoside, such as a C8-C20 glucoside.

1.23 Composition 1.22, wherein the surfactant is decyl glucoside.

1.24 Any foregoing composition, wherein the surfactant is a fatty acyl amide or fatty acyl ester carboxylate or sulfonate, e.g., an N-fatty acyl-N-alkyl taurate salt, or an N-fatty acyl glycinate salt (e.g., N-cocoyl glycine salt), or an N-fatty acyl glutamate salt (e.g., N-cocoyl glutamate salt), or an N-fatty acyl-N-alkyl glycinate salt (e.g., N-cocoyl N-methyl glycine salt), or an N-fatty acyl-N-alkyl glutamate salt (e.g., N-cocoyl N-methyl glutamate salt), or an O-fatty acyl isethionate salt (e.g., a cocoyl isethionate salt), or a mono- or di-($C_{12-20}$alkyl) sulfosuccinate salt (e.g., a dioctyl sulfosuccinate salt), wherein any such salt is optionally or sodium or potassium salt.

1.25 Composition 1.24, wherein the surfactant is an N-fatty acyl-N-alkyl taurate salt (e.g., sodium or potassium salt).

1.26 Composition 1.25, wherein the surfactant is an N-cocoyl N-methyl taurate salt (e.g., sodium ethyl cocoyl taurate).

1.27 Any foregoing composition wherein the surfactant is present in an amount sufficient to substantially interfere with interaction between the guanide agent and the short chain linear polyphosphate salt, e.g., an amount sufficient to inhibit formation of a precipitate or reduction of the efficacy of the guanide agent, or sufficient to form micelles (e.g., comprising the guanide agent).

1.28 Any foregoing composition wherein the surfactant is present in an amount of 0.01 to 5.0%, 0.1 to 2.0%, 0.1 to 1.0%, 0.1 to 0.5%, 0.2 to 0.4%, 0.3 to 0.4%, 0.31% to 0.35%, 0.32 to 0.35%, 0.31% to 0.33%, 0.32 to 0.33%, 0.3 to 0.5%, 0.3 to 0.6%, 0.4 to 2%, 0.4 to 1.5%, 0.4 to 1.0%, 0.4 to 0.8%, 0.4 to 0.6%, 0.4 to 0.5%, 0.5 to 2.0%, 0.5 to 1.5%, 0.5 to 1.0%, 0.75 to 1.5%, 0.9% to 1.3%, 0.95% to 1.2%, 0.98% to 1.1%, 1.0 to 3.0%, 1.0 to 2.0%, 1.0 to 1.5%, or about 0.32%, about 0.45%, about 0.5%, about 0.6%, about 0.75%, about 1.0%, about 1.25%, about 1.5%, or about 2.0%, based on the total weight of the composition.

1.29 Any foregoing composition, wherein the composition comprises two or more of a zwitterionic, cationic, or nonionic surfactant, or a fatty acyl amide alkyl sulfonate surfactant, for example: a zwitterionic surfactant and a nonionic surfactant, or a cationic surfactant and nonionic surfactant, or a fatty acyl amide alkyl sulfonate surfactant and a nonionic surfactant, or two different nonionic surfactants.

1.30 Any foregoing composition, wherein the composition further comprises a poloxamer surfactant (e.g., poloxamer 407).

1.31 Any foregoing composition, wherein the composition comprises greater than 50% water, based on the total weight of the composition.

1.32 Any foregoing composition, wherein the composition comprises 70% to 95% water, e.g., 70% to 90%, or 70% to 80%, based on the total weight of the composition.

1.33 Any foregoing composition, wherein the composition comprises one or more of a thickener, a buffer (e.g., a hydroxide base or an organic acid such as citric acid), a humectant (e.g., sorbitol, glycerin, propylene glycol), an abrasive, a sweetener, a flavorant, a pigment, a dye, an anti-caries agent (e.g., a fluoride source), an antibacterial agent, a whitening agent, a desensitizing agent, a preservative benzyl alcohol or benzoic acid) an amino acid (lysine or arginine), or a mixture thereof.

1.34 Composition 1.33, wherein the composition comprises a phosphate buffer.

1.35 Composition 1.33, wherein the composition comprises a buffer selected from sodium hydroxide and potassium hydroxide, 1.36 Composition 1.33, wherein the composition comprises a buffer selected from lactic acid, citric acid, hydrochloric acid, glycolic acid, sodium hydroxide, potassium chloride, monosodium citrate, disodium citrate, monosodium malate, sodium carbonate, bicarbonates, sesquicarbonates, borates, silicates, monosodium phosphate, trisodium phosphate, pyrophosphate salts, imidazole, or combinations thereof; e.g., citric acid.

1.37 Any foregoing composition wherein the composition has a pH of about 4 to 9, about 5 to 8, about 5.5 to 7, or about 5.5 to 6.5, or about 6 to 7, or about 6 to 6.5, or about 6.05 to 6.25, or about 6.10 to 6.20, or about 6.12 to 6.19, or about 6.0 to 6.25, or about 6.0 to 6.15, or about 6.0 to 6.10.

1.38 Any foregoing composition wherein the composition comprises a humectant mixture comprising two or more of sorbitol, propylene glycol, and glycerin.

1.39 Any foregoing composition wherein the composition comprises a humectant, wherein the humectant is a mixture of glycerin, sorbitol, and propylene glycol.

1.40 Any foregoing composition, wherein the composition comprises the humectants in a combined amount of 10 to 40% by weight of the composition, e.g., in an amount of 20 to 40% or 30 to 40%.

1.41 Composition 1.40, wherein the composition comprises glycerin, sorbitol and propylene glycol each in an amount of 5-10%, e.g., 7-10%.

1.42 Any foregoing composition wherein the composition comprises a sweetener.

1.43 Any foregoing composition wherein the composition comprises a sweetener, wherein the sweetener is sodium saccharin.

1.44 Any foregoing composition wherein the composition comprises a flavorant.

1.45 Any foregoing composition wherein the composition comprises a dye, e.g., FD&C Blue No. 1.

1.46 Any foregoing composition wherein the composition comprises an anti-caries agent.

1.47 Any foregoing composition wherein the composition comprises a fluoride ion source.

1.48 Any foregoing composition wherein the composition comprises a fluoride ion source, wherein the fluoride ion source is stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N-tris(2-ethanol)-dihydrofluoride), ammonium fluoride, titanium fluoride, hexafluorosulfate, or a mixture thereof.

1.49 Any foregoing composition wherein the composition is a mouthwash.

1.50 Any foregoing composition which is biphasic, e.g., wherein the solution comprises two distinct aqueous phases having different composition and density.

1.51 Any foregoing composition which comprises less than 5%, e.g., less than 2% of hydrophobic ingredients.

1.52 Any foregoing composition which is essentially oil-free, apart from flavoring agents.

1.53 Any foregoing composition wherein there is no visible precipitation or reaction between the short chain polyphosphate salt and the orally acceptable cationic active agent after three months of storage at room temperature.

1.54 Composition 1 or any of 1.1-1.53, wherein the composition is a mouthwash comprising from 0.1 to 0.5 wt. % of chlorhexidine (e.g., chlorhexidine digluconate), 1.0 wt. % to 2 wt. % of sodium tripolyphosphate, and 0.95% to 1.2% of an alkyl polyglucoside, such as a C8-C20 glucoside (e.g., decyl glucoside), based on the total weight of the composition.

1.55 Composition 1.54, wherein the pH of the composition is 5.5-7.0.

1.56 Composition 1 or any of 1.1-1.53, wherein the composition is a mouthwash comprising from 0.1 to 0.5 wt. % of chlorhexidine (e.g., chlorhexidine digluconate), 1.0 wt. % to 2 wt. % of sodium tripolyphosphate, and 0.32 to 0.35% of cocamidopropyl betaine, based on the total weight of the composition.

1.57 Composition 1.56, wherein the pH of the composition is 6.1 to 6.2 (e.g., 6.12-6.19).

1.58 Composition 1 or any of 1.1-1.53, wherein the composition is a mouthwash comprising from 0.1 to 0.5 wt. % of chlorhexidine (e.g., chlorhexidine digluconate), 1.0 wt. % to 2 wt. % of sodium tripolyphosphate, and 0.3 to 0.6% of an N-cocoyl N-methyl taurate salt (e.g., sodium methyl cocoyl taurate), based on the total weight of the composition.

1.59 Composition 1 or any of 1.1-1.53, wherein the composition is a mouthwash comprising from 0.1 to 0.5 wt. % of chlorhexidine (e.g., chlorhexidine digluconate), 1.0 wt. % to 2 wt. % of sodium tripolyphosphate, and 0.4 to 0.5% of an N-cocoyl N-methyl taurate salt (e.g., sodium methyl cocoyl taurate), based on the total weight of the composition.

1.60 Composition 1 or any of 1.1-1.53, wherein the composition is a mouthwash comprising from 0.1 to 0.5 wt. % of chlorhexidine (e.g., chlorhexidine digluconate), 1.0 wt. % to 2 wt. % of sodium tripolyphosphate, and 0.5 to 1.0% of cetylpyridinium chloride, based on the total weight of the composition.

1.61 Composition 1.56, wherein the pH of the composition is 6.0 to 6.1.

The disclosure further provides the use of stabilizing amount of a zwitterionic, cationic, or nonionic surfactant, or a fatty acyl amide alkyl sulfonate surfactant, or a combination thereof, to stabilize an oral care formulation comprising a short chain linear polyphosphate salt and an effective amount of orally acceptable guanide antibacterial agent, for example, for use in any of the foregoing Compositions 1, et seq.

As used herein, the term "surfactant" is equivalent to the term "emulsifier" as these terms are used in the art.

As used herein, an "oral care composition" refers to a composition for which the intended use can include oral care, oral hygiene, or oral appearance, or for which the intended method of use can comprise administration to the oral cavity. The term "oral care composition" thus specifically excludes compositions which are highly toxic, unpalatable, or otherwise unsuitable for administration to the oral cavity. In some embodiments, an oral care composition is not intentionally swallowed, but is rather retained in the oral cavity for a time sufficient to affect the intended utility. The oral care compositions as disclosed herein may be used in nonhuman mammals such as companion animals (e.g., dogs and cats), as well as by humans. In some embodiments, the oral care compositions as disclosed herein are used by humans. Oral care compositions include, for example, dentifrice and mouthwash. In some embodiments, the disclosure provides mouthwash formulations.

As used herein, "orally acceptable" refers to a material that is safe and palatable at the relevant concentrations for use in an oral care formulation, such as a mouthwash or dentifrice.

As used herein, "orally acceptable carrier" refers to any vehicle useful in formulating the oral care compositions disclosed herein. The orally acceptable carrier is not harmful to a mammal in amounts disclosed herein when retained in the mouth, without swallowing, for a period sufficient to permit effective contact with a dental surface as required herein. In general, the orally acceptable carrier is not harmful even if unintentionally swallowed. Suitable orally acceptable carriers include, for example, one or more of the following: water, a thickener, a buffer, a humectant, a surfactant, an abrasive, a sweetener, a flavorant, a pigment, a dye, an anti-caries agent, an anti-bacterial, a whitening agent, a desensitizing agent, a vitamin, a preservative, an enzyme, and mixtures thereof.

As used herein, "short chain polyphosphate salt" encompasses orally acceptable mono- and polyphosphates, for example, $P_{1-6}$ phosphates such as monobasic, dibasic or tribasic orthophosphate; and dimeric phosphates, e.g., sodium hexametaphosphate. For example, the short chain polyphosphate salt may comprise alkali dibasic orthophosphate and alkali pyrophosphate salts, e.g., selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, and mixtures of any of two or more of these. In a particular embodiment, for example the compositions comprise a mixture of tetrasodium pyrophosphate ($Na_4P_2O_7$), calcium pyrophosphate ($Ca_2P_2O_7$), and sodium phosphate dibasic ($Na_2HPO_4$). In one embodiment, tetrasodium pyrophosphate (TSPP), sodium tripolyphosphate (STPP), tetrapotassium pyrophosphate (TKPP), or mixtures thereof are used. In another embodiment, the compositions comprise a mixture of tetrapotassium pyrophosphate (TSPP) and sodium tripolyphosphate (STPP) ($Na_5P_3O_{10}$). Such phosphates are provided in an amount effective to reduce stains on tooth surfaces, erosion of the enamel, to aid in cleaning the teeth, and/or reduce tartar buildup on the teeth, for example, in an amount of 0.01 wt. % to 5.0 wt. %, 0.1 wt. % to 5.0 wt. %, 0.1 wt. % to 3 wt. %, 0.5 wt. % to 1.5 wt. %, or 1.0 wt. % based on the total weight of the composition.

As used herein, "fatty acyl amide alkyl sulfonate surfactant" means those surface-active or detergent compounds that contain an organic hydrophobic fatty acyl group, e.g., C8-26 or C10-18, attached to a tertiary amide nitrogen atom, which nitrogen atom is attached to a linear C2-20 alkyl chain terminated with a sulfonic acid group in free or salt form, so as to form a water-soluble detergent. Such surfactants are employed in the form of water-soluble salts and the salt-forming cation usually is selected from sodium, potassium, ammonium, magnesium and mono-, di- or tri-$C_2$-$C_3$ alkanolammonium, with the sodium, magnesium and ammonium cations again being the usual ones chosen. In certain embodiments, the anionic surfactant is present in an amount of 0.01 to 5.0%, 0.1 to 2.0%, 0.2 to 0.4%, or about 0.33%.

As used herein, the term "fatty acid" or "fatty acyl" refers to the derivative of a natural fatty acid, e.g., a C4-C28 saturated or unsaturated fatty acid, and this includes partially hydrogenated derivatives thereof. Preferably, the fatty acid root is a C8-C26 fatty acid, or a C12-18 fatty acid, such as one derived from caprylic acid, capric acid, lauric acid, stearic acid, myristoleic acid, palmitoleic acid, sapienic acid, oleic acid, linoleic acid, and linolenic acid. As used herein, "cocoyl" or "cocoate" refers to the acyl group nominally derived from cocoic acid, which is the name for the mixture of fatty acids predominant in coconut oil, primarily lauric acid, myristic acid, palmitic acid, decanoic acid, oleic acid and caprylic acid.

As used herein, "nonionic surfactant" generally refers to compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name PLURONIC®), polyoxyethylene, polyoxyethylene sorbitan esters (sold under trade name TWEENS®), Polyoxyl hydrogenated castor oils (e.g., polyoxyl 40 hydrogenated castor oil or polyoxyl 60 hydrogenated castor oil), fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, alkyl polyglycosides (for example, fatty alcohol ethers of polyglycosides, such as fatty alcohol ethers of polyglucosides, e.g., decyl, lauryl, capryl, caprylyl, myristyl, stearyl and other ethers of glucose and polyglucoside polymers, including mixed ethers such as capryl/caprylyl ($C_{8-10}$) glucoside, coco ($C_{8-16}$) glucoside, and lauryl ($C_{12-16}$) glucoside), long chain tertiary amine oxides, long chain tertiary phosphine oxides, long chain dialkyl sulfoxides, and mixtures of such materials.

In some embodiments, the nonionic surfactant comprises amine oxides, fatty acid amides, ethoxylated fatty alcohols, block copolymers of polyethylene glycol and polypropylene glycol, glycerol alkyl esters, polyoxyethytene glycol octylphenol ethers, sorbitan alkyl esters, polyoxyethylene glycol sorbitan alkyl esters, and mixtures thereof. Examples of amine oxides include, but are not limited to, laurylamidopropyl dimethylamine oxide, myristylamidopropyl dimethylamine oxide, and mixtures thereof. Examples of fatty acid amides include, but are not limited to, cocomonoethanolamide, lauramide monoethanolamide, cocodiethanolamide, and mixtures thereof. In certain embodiments, the nonionic surfactant is a combination of an amine oxide and a fatty acid amide. In certain embodiments, the amine oxide is a mixture of laurylamidopropyl dimethylamine oxide and myristylamidopropyl dimethylamine oxide. In certain embodiments, the nonionic surfactant is a combination of lauryl/myristylamidopropyl dimethylamine oxide and cocomonoethanolamide. In certain embodiments, the nonionic surfactant is present in an amount of 0.01 to 5.0%, 0.1 to 2.0%, 0.1 to 0.6%, 0.2 to 0.4%, about 0.2%, or about 0.5%.

As used herein, the term "cationic surfactant" includes the cationic surfactants disclosed in WO 2007/011552A2, the contents of which are incorporated herein by reference in its entirety. Amino-acid based cationic surfactants also include those disclosed in Roy et al., *Langmuir* 21, 10398-10404 (2005).

As used herein, "biphasic" refers to stable liquid compositions which contain at least two distinct homogeneous phases, having different densities, such that the phases are separate at rest. The phases may be readily mixed by shaking but will then re-separate over a short period, e.g., less than half an hour. In certain embodiments, the term excludes gels, emulsions, microemulsions, and homogeneous solutions. In certain embodiments, these formulations differ from conventional biphasic formulations in that both phases are aqueous, rather than one phase being hydrophobic and the other hydrophilic.

As used herein, a "tartar control agent" refers to a compound or a mixture of compounds that inhibit the formation of tartar, a mixture of calcium phosphates on organic matrices, and/or the deposition of plaque on teeth to form tartar (calculus).

As used herein, "chemical stain" refers to a discoloration of a dental surface caused by adsorption or absorption of a colored agent on or into the surface, or caused by chemical reaction of material of the dental surface (e.g., dental enamel) with a colored or noncolored agent contacting the surface. "Chemical staining" herein means formation and/or development of a chemical stain.

As used herein, "dental surface" refers to a surface of a natural tooth or a hard surface of artificial dentition including a crown, cap, filling, bridge, dental implant and the like. In some embodiments, the dental surface is a natural tooth.

The compositions are, for example, oral care compositions, in accordance with Composition 1, et seq. for example mouthwashes. Any of the compositions of Composition 1, et seq. is suitable for oral care use, provided the ingredients are orally acceptable.

The oral care composition used in the present disclosure comprise significant levels of water. Water employed in the preparation of commercial oral compositions should be deionized and free of organic impurities. The amount of water in the compositions includes the free water that is added plus that amount which is introduced with other materials.

Mouthwashes frequently contain significant levels of ethanol, which is often needed to solubilize essential oils and to prevent bacterial contamination. High levels of ethanol may be undesirable, because in addition to the potential for abuse by ingestion, the ethanol may exacerbate conditions like xerostomia. Accordingly, in some embodiments, the oral care compositions of the invention are substantially free of ethanol, e.g., contain less than 1% ethanol or less than 0.1% ethanol.

Humectants can enhance the viscosity, mouthfeel, and sweetness of the product, and may also help preserve the product from degradation or microbial contamination. Suitable humectants include edible polyhydric alcohols such as glycerin, sorbitol, xylitol, propylene glycol as well as other polyols and mixtures of these humectants. Sorbitol may in some cases be provided as a hydrogenated starch hydrolysate in syrup form, which comprises primarily sorbitol (the product if the starch were completely hydrolyzed to glucose, then hydrogenated), but due to incomplete hydrolysis and/or presence of saccharides other than glucose, may also include other sugar alcohols such mannitol, maltitol, and longer chain hydrogenated saccharides, and these other sugar alcohols also function as humectants in this case. Thus, the sorbitol may be provided as an about 70 wt. % aqueous solution.

Flavorings for use in the present invention may include extracts or oils from flavorful plants such as peppermint, spearmint, cinnamon, wintergreen, and combinations thereof, cooling agents such as menthol, methyl salicylate, and commercially available products such as OptaCool® from Symrise, as well as sweeteners, which may include polyols (which also function as humectants), saccharin, acesulfame, aspartame, neotame, stevia and sucralose.

Further provided is a method (Method A) for the treatment and/or inhibition of a chemical stain, plaque, and/or tartar on a dental surface, comprising contacting the dental surface with any of the preceding oral care compositions.

Further provided herein is Method A as follows:
A.1 Method A wherein the composition is Composition 1, e.g., selected from any of Compositions 1.1-1.61.
A.2 Method A or A.1 wherein the method is for the treatment of a chemical stain, plaque, and/or tartar on the dental surface.
A.3 Method A.2 wherein the method is for the treatment of a chemical stain on the dental surface.
A.4 Method A.2 wherein the method is for the treatment of plaque on the dental surface.
A.5 Method A.2 wherein the method is for the treatment of tartar on the dental surface.
A.6 Method A or A.1 wherein the method is for the inhibition of a chemical stain, plaque, and/or tartar on the dental surface.
A.7 Method A.6 wherein the method is for the inhibition of a chemical stain on the dental surface.
A.8 Method A.6 wherein the method is for the inhibition of plaque on the dental surface.
A.9 Method A.6 wherein the method is for the inhibition of tartar on the dental surface.
A.10 Method A or A.1-A.9 wherein the dental surface is a human tooth.
A.11 Method A or A.1-A.10 wherein the composition is contacted with the dental surface by brushing.
A.12 Any foregoing Method A, et seq. wherein the formulation s biphasic and is shaken before use.

Further provided is a method (Method B) for the treatment and/or inhibition of gum disease comprising contacting the oral cavity with any of the preceding oral care compositions.

Further provided herein is Method B as follows:
B.1 Method B wherein the composition is Composition 1, e.g., any of Compositions 1.1-1.61.
B.2 Method B or B.1 wherein the method is for the treatment of gum disease.
B.3 Method B, B.1, or B.2 wherein the gum disease is gingivitis.
B.4 Method B, B.1, or B wherein the gum disease is periodontitis.
B.5 Method B or B.1 wherein the method is for the inhibition of gum disease.
B.6 Method B, B.1, or B.5 wherein the gum disease is gingivitis.
B.7 Method B, B.1, or B.5 wherein the gum disease is periodontitis.
B.8 Method B or B.1-B.7 wherein the oral cavity is a human oral cavity.
B.9 Method B or B.1-B.8 wherein the composition is contacted with the oral cavity by brushing.
B.10 Any foregoing Method B, et seq. wherein the formulation is biphasic and is shaken before use.

Further provided is a method (Method C) for the treatment and/or inhibition of halitosis comprising contacting the oral cavity with any of the preceding oral care compositions.

Further provided herein is Method C as follows:
C.1 Method C wherein the composition is Composition 1, e.g., any of Compositions 1.1-1.61.
C.2 Method C or C.1 wherein the oral cavity is a human oral cavity.
C.3 Method C, C.1, or C.2 wherein the composition is contacted with the oral cavity by brushing.
C.4 Any foregoing Method C, et seq. wherein the formulation is biphasic and is shaken before use.

Further provided is a method (Method D) for inhibiting biofilm formation on a dental surface comprising contacting the dental surface with any of the preceding oral care compositions.

Further provided herein is Method D as follows:
D.1 Method D wherein the composition is Composition 1, e.g., any of Compositions 1.1-1.61.
D.2 Method D or D.1 wherein the dental surface is a human tooth.
D.3 Method D, D.1, or D.2 wherein the composition is contacted with the dental surface by brushing.
D.4 Any foregoing Method), et seq. wherein the formulation is biphasic and is shaken before use.

Further provided is a method (Method E) for treating and/or inhibiting bacteria from aggregating and forming bigger colonies in an oral cavity comprising contacting the oral cavity with any of the preceding oral care compositions.

Further provided herein is Method E as follows:
E.1 Method E wherein the composition is Composition 1, e.g., any of Compositions 1.1-1.61.
E.2 Method E or E.1 wherein the oral cavity is a human oral cavity.
E.3 Method E, E.1, or E.2 wherein the composition is contacted with the oral cavity by brushing.
E.4 Any foregoing Method E, et seq. wherein the formulation is biphasic and is shaken before use.

Further provided are Compositions 1, et seq. for use in any of Methods A-E.

As used herein, "inhibition" refers to reduction of stains that would otherwise form or develop subsequent to the time of the treatment. Such inhibition can range from a small but observable or measurable reduction to complete inhibition of subsequent staining, by comparison with an untreated or placebo-treated dental surface.

Where the dental surface is substantially free of chemical stains, Method A, e.g., A.1-A.12, is effective to inhibit formation and development of new chemical stains, as can occur for example by oral use of tobacco products (including smoking) or by drinking tea, coffee, red wine, or cola beverages, subsequent to treatment according to the method. Where the dental surface already possesses some degree of chemical staining, Method A, e.g., A.1-A.12, is effective to inhibit further development of the existing stain. In some embodiments, the Method A, e.g., A.1-A.12, can remove, partially or completely, an existing chemical stain as well as inhibit subsequent staining.

EXAMPLES

Example 1—Chlorhexidine, STPP and Nonionic Surfactant

Chlorhexidine (CHX) mouthwash is very effective to fight gingivitis. But after CHX has been adsorbed to a tooth surface, stains often result after drinking coffee, tea, or red wine, primarily occurring through charge interaction between the positively charged CHX and negatively charged stains. This means that someone using a chlorhexidine must either avoid foods and beverages with a dark color, or become accustomed to teeth that are more yellow and stained.

Sodium tripolyphosphate (STPP) exhibits significant stain fighting ability, and when used in oral care products, deposits onto a tooth surface. However, when STPP and CHX are combined, complexes formed by the two can result in precipitation of both STPP and CHX, inactivating both components.

It has been unexpectedly found that CHX and STPP can be formulated in such a way to prevent precipitation (or to re-dissolve the precipitate) through the inclusion of the mild, nonionic surfactant decyl glucoside (an alkyl polyglucoside, or APG).

Micelles of CHX stabilized with APG are generally formed by making an aqueous solution of 0.2% CHX, adding the appropriate amount of APG, followed by addition of 1.6% of STPP, and an appropriate amount of citric acid to bring the solution pH to the range of 5.5-7. Preferably, the APG surfactant is added before CHX and STPP are combined. This is because CHX and STPP, when combined in aqueous solution, will form an insoluble complex. If APG is added once this complex has formed, under some circumstances, an insoluble coacervate may form.

For the following experiments, a 0.2 wt. % aqueous solution of chlorhexidine gluconate, and a 10.0 wt. % aqueous solution of decyl glucoside ("APG") are prepared. The pH of the decyl glucoside solution is adjusted to 5.5-7.0 using citric acid. Seven formulations are prepared, as shown in Table 1. For each formulation, the appropriate amount of the decyl glucoside solution is added to appropriate amounts of the chlorhexidine stock solution. STPP is then added to each formulation, and the mixture is agitated by a bath sonicator until no large solids remained. Additional citric acid is added to adjust the pH to 5.5-7.0. The formulations are then agitated for an additional five minutes, then allowed to equilibrate for 30 minutes before observation and transmittance measurements.

TABLE 1

| Formulation | CHX (Wt. %) | APG (Wt. %) | STPP (Wt. %) | pH | Transmittance (%) | Visual |
|---|---|---|---|---|---|---|
| 1-1 | 0.20% | 0.75% | 1.60% | 6.39 | 21 | Opaque solution |
| 1-2 | 0.20% | 0.82% | 1.60% | 6.76 | 21 | Opaque solution |
| 1-3 | 0.20% | 0.85% | 1.60% | 6.59 | 25 | Opaque solution |
| 1-4 | 0.20% | 0.92% | 1.60% | 6.31 | 85 | Opaque solution |
| 1-5 | 0.20% | 0.98% | 1.60% | 6.33 | 99 | Clear solution |
| 1-6 | 0.20% | 1.00% | 1.60% | 6.76 | 92 | Clear solution |
| 1-7 | 0.20% | 1.10% | 1.60% | 5.96 | 99 | Clear solution |

The transmittance of DI water was calibrated to 100 before the measurements were taken. The results show that at or below 0.92% of APG, the mixture is a milky white suspension. While above 0.92% of APG, the mixture is a stable, clear solution.

Antimicrobial activity of the formulations is tested to determine whether the chlorhexidine is fully active. The Alamar blue test for antimicrobial activity is conducted according to standard methodology. Bacteria inoculum is prepared by diluting fresh saliva 2× with deionized water, followed by centrifugation at 8000 G/25° C. for 10 min, and decanting the upper clear liquid into a glass jar. The negative control (A) is distilled water. The positive control (B) is 2 wt. % chlorhexidine gluconate solution. The APG control (C) is a 10 wt. % decyl glucoside solution. The two test solutions are: (D) 2 wt. % chlorhexidine gluconate with 10 wt. % decyl glucoside; and (E) 2 wt. % chlorhexidine gluconate with 10 wt. % decyl glucoside solution, with 14% w/w STPP added. Each of the test solutions is combined with saliva in a weight ratio of 1:10 (solution to saliva). The pH of each mixture is adjusted to 5.5-7 by adding citric acid. The mixtures are vortexed for 1 minute, and incubated at 37° C. for 30 minutes. Subsequent addition of 200 µL of Alamar Blue dye immediately produced blue color in all samples and pictures were taken for comparison at different time intervals (0 hours, 24 hours, 48 hours) to show the evolution of color development. A blue color indicates bacterial kill in saliva and no bacterial growth, while a pink color indicates viable bacteria are still present. An in-between color, such as purple, suggests that bacteria are beginning to grow back. The results are shown in the table below:

| Observation Time: | Sample (A) (D.I. contr) | Sample (B) (CHX contr) | Sample (C) (APG contr) | Sample (D) (CHX/APG) | Sample (E) (CHX/APG/STPP) |
|---|---|---|---|---|---|
| 0 Hours | Clear bright blue | Hazy bright blue | Clear bright blue | Clear bright blue | Clear bright blue |
| 24 Hours | Clear bright pink | Hazy bright blue | Hazy light purple | Clear pale blue | Hazy bright blue |
| 48 Hours | Clear bright pink | Hazy bright blue | Clear bright pink | Clear pale blue | Hazy bright blue |

The results show that the negative control retained a clear pink color after overnight incubation. APG negative control showed a color change from blue to pink after two days. Both the APG-CHX mixture and the APG-CHX-STPP mixture showed approximately the same level of antibacterial activity as the CHX positive control.

These results demonstrate that APG alone can stabilize CHX and STPP in an aqueous system and keep the solution clear at concentrations greater than 0.99%, preventing the interactions between the cationic CHX and the anionic STPP. At a 0.2% concentration, the APG-stabilized CHX remains effective against bacteria, with or without the STPP. Thus, APG can be used in mouthwash products to stabilize the CHX, which provides antibacterial properties, and with STPP to provide anti-staining benefits. The formula is therefore mild, and lacks the potentially harsh and irritating effects from other surfactants.

Example 2—Chlorhexidine, STPP and Zwitterionic Surfactant

It has been unexpectedly found that CHX and STPP can be formulated in such a way to prevent precipitation (or to re-dissolve the precipitate) through the inclusion of the mild, zwitterionic surfactant cocamidopropyl betaine CAPB).

Micelles of CHX stabilized with CAPB are generally formed by making an aqueous solution of 0.2% CHX with 1.6% STPP, adding the appropriate amount of CAPB, and an appropriate amount of citric acid to bring the solution pH to the range of 6.12-6.19. It is unexpectedly found that from an initial pH of 9, as the pH lowered towards 6.2 the mixtures change from milky suspensions to clear solutions.

For the following experiments, a 0.2 wt. % aqueous solution of chlorhexidine gluconate, and a 2.0 wt. % aqueous solution of CAPB are prepared. STPP is added to the chlorhexidine solution to provide 1.6 wt. % STPP. Five formulations are prepared, as shown in Table 2. For each formulation, the appropriate amount of the CAPB solution is added to appropriate amounts of the chlorhexidine/STPP stock solution. The mixture is agitated by a bath sonicator, and then additional citric acid is added to adjust the pH to 6.12-6.19. The formulations are then agitated for an additional five minutes, then allowed to equilibrate for 18 hours before observation. It is noted that solutions 2-2 and 2-3 were clear as formulated, but gradually formed a precipitate over the course of several hours. In each case where a precipitate formed, it had completely settled to the bottom of the test vials by the time of observation. In a second experimental run, two formulations having 0.33% CAPB are compared, with one pH adjusted to 6.19, and the other not adjusted (pH 9.1). The solution without pH adjustment is very opaque, but without visible precipitated solids, and remains so after 18 hours.

TABLE 2

| Formulation | CHX (Wt. %) | CAPB (Wt. %) | STPP (Wt. %) | pH | Visual |
|---|---|---|---|---|---|
| 2-1 | 0.20% | 0.29% | 1.60% | 6.12 | Clear solution, substantial precipitate |
| 2-2 | 0.20% | 0.30% | 1.60% | 6.14 | Clear solution, substantial precipitate |
| 2-3 | 0.20% | 0.31% | 1.60% | 6.12 | Clear solution, slight precipitate |
| 2-4 | 0.20% | 0.32% | 1.60% | 6.19 | Clear solution, no solids |
| 2-5 | 0.20% | 0.33% | 1.60% | 6.19 | Clear solution, no solids |
| 2-6 | 0.20% | 0.33% | 1.60% | 6.19 | Clear solution, no solids |
| 2-7 | 0.20% | 0.33% | 1.60% | 9.1 | Opaque solution, no settled solids |

The results show that below 0.32% of CAPB, the mixtures form a precipitate on standing, while at or above 0.32% of CAPB, the mixture is a stable, clear solution, if formulated at a pH of less than 7, e.g., 6.12 to 6.19.

Antimicrobial activity of the formulations is tested using the Alamar blue test as described in Example 1. The negative control (A) is distilled water. The positive control (B) is 2 wt. % chlorhexidine gluconate solution. The CAPB control (C) is 3.3 wt. % CAPB solution. The two test solutions are: (D) 2 wt. % chlorhexidine gluconate with 3.3 wt. % CAPB; and (E) 2 wt. % chlorhexidine gluconate with 3.3 wt. % CAPB solution, with 14% w/w STPP added. Each of the test solutions is combined with saliva in a weight ratio of 1:10 (solution to saliva). The pH of each mixture is adjusted to 5.5-7 by adding citric acid. The mixtures are vortexed for 1 minute, and incubated at 37° C. for 30 minutes. Subsequent addition of 200 μL of Alamar Blue dye immediately produced blue color in all samples and pictures were taken for comparison at different time intervals (0 hours, 24 hours, 48 hours) to show the evolution of color development. A blue color indicates bacterial kill in saliva and no bacterial growth, while a pink color indicates viable bacteria are still present. An in-between color, such as purple, suggests that bacteria are beginning to grow back. The results are shown in the table below:

| Observation Time: | Sample (A) (D.I. contr) | Sample (B) (CHX contr) | Sample (C) (CAPB contr) | Sample (D) (CHX/CAPB) | Sample (E) (CHX/CAPB/STPP) |
|---|---|---|---|---|---|
| 0 Hours | Clear bright blue | Hazy bright blue | Clear bright blue | Hazy bright blue | Hazy bright blue |
| 24 Hours | Clear bright pink | Hazy bright blue | Hazy bright blue | Hazy pale blue | Hazy bright blue |
| 48 Hours | Clear bright pink | Hazy bright blue | Clear bright pink | Hazy pale blue | Hazy bright blue |

The results show that the negative control retained a clear pink color after overnight incubation. CAPB negative control showed a color change from blue to pink after two days. Both the CAPB-CHX mixture and the CAPB-CHX-STPP mixture showed approximately the same level of antibacterial activity as the CHX positive control.

These results demonstrate that CAPB alone can stabilize CHX and STPP in an aqueous system and keep the solution clear at concentrations greater than 0.31% at a pH of 6.1 to 6.2, preventing the interactions between the cationic CHX and the anionic STPP. At a 0.2% concentration, the CAPB-stabilized CHX remains effective against bacteria, with or without the STPP. Thus, CAPB can be used in mouthwash products to stabilize the CHX, which provides antibacterial properties, and with STPP to provide anti-staining benefits. The formula is therefore mild, and lacks the potentially harsh and irritating effects from other surfactants.

Example 3—Chlorhexidine, STPP and Sodium Methyl Cocoyl Taurate Surfactant

It has been previously shown that the anionic surfactant sodium lauryl sulfate (SLS) can stabilize a CHX-STPP mouthwash formulation by formation of micelles. However, it has also been found that such solutions are not crystal clear, but rather are somewhat opaque. Under colder conditions, the opacity of the solutions becomes even worse. Without being bound by theory, it is believed that these clarity issues are due to the large size of the micelles formed between CHX and SLS.

It has been unexpectedly found that the mild, anionic surfactant sodium methyl cocoyl taurate ("Taurate") is able to stabilize CHX in solution with improved clarity.

Two mouthwash solution are prepared according to Table 3, below, one using SLS as stabilizer and the other using Taurate.

TABLE 3

Test formulations

| Materials | Formulation 3-1 (wt. %) | Formulation 3-2 (wt. %) |
|---|---|---|
| Chlorhexidine digluconate (19% w/v solution) | 1.0 | 1.0 |
| Poloxamer 407 (nonionic surfactant) | 0.33 | 0.33 |
| Sodium Tripolyphosphate | 1.66 | 1.66 |
| Sodium lauryl sulfate | 0.45 | — |
| Taurate | — | 0.45 |

TABLE 3-continued

Test formulations

| Materials | Formulation 3-1 (wt. %) | Formulation 3-2 (wt. %) |
|---|---|---|
| Glycerin | 7.2 | 7.2 |
| Sorbitol (70% solution) | 9.6 (6.7 active) | 9.6 (6.7 active) |
| Propylene Glycol | 7.0 | 7.0 |
| Flavors/Sweeteners | 0.17 | 0.17 |
| Colorant | 0.0001 | 0.0001 |
| Citric Acid | 0.37 | 0.37 |
| Preservative | 0.25 | 0.25 |
| Water | q.s. (~72) | q.s. (~72) |

It is found that Formulation 3-2 is clear and colorless, but Formulation 3-1 is significantly opaque.

To evaluate the stability of the solutions to freeze-thaw, each solution is subjected to three cycles of freezing to −30° C. for 24 hours followed by thawing back to room temperature for 24 hours. It is found that Formulation 3-2 remains clear and colorless after the three freeze-thaw cycles, but Formulation 3-1 is completely opaque (much more so than initially).

To further evaluate the effect of the Taurate concentration, additional Formulations 3-3, 3-4, 3-5, 3-6 and 3-7 are prepared, having, respectively, 0.1 wt. % Taurate, 0.2 wt. % Taurate, 0.25%, 0.35% Taurate or 0.45 wt. % Taurate (the remaining balance of material is water). Formulation 3-7 is therefore identical to Formulation 3-2, but was prepared side by side with Formulations 3-3 to 3-6 by adding Taurate to the otherwise complete mouthwash formulation.

| Formulation | CHX (Wt. %) | Taurate (Wt. %) | STPP (Wt. %) | Transmittance (%) | Visual |
|---|---|---|---|---|---|
| 3-3 | 0.2% | 0.1% | 1.66% | 18 | Very opaque solution |
| 3-4 | 0.2% | 0.2% | 1.66% | 18 | Very opaque solution |
| 3-5 | 0.2% | 0.25% | 1.66% | 65 | Somewhat opaque solution |
| 3-6 | 0.2% | 0.35% | 1.66% | 90 | Clear solution |
| 3-7 | 0.2% | 0.45% | 1.66% | 95 | Clear solution |

It is found that the 0.1% Taurate solution is strongly opaque with a significant amount of visible white precipitate settled to the bottom. The 0.2% and 0.25% Taurate solutions are less opaque and have less white precipitate than the 0.1% Taurate solution. The 0.35% Taurate solution is somewhat opaque but without any precipitated solid. Only the 0.45% Taurate solution is clear and colorless without precipitated solid. These observations are consistent with the transmittance results.

An assay is conducted on the 0.45% Taurate Formulation 3-2 to determine the amount of free CHX present. It is found that the amount of free CHX is 0.18 wt. %, which is only slightly below the calculated theoretical value of 0.19%.

Example 4—Chlorhexidine, STPP and Cationic Surfactant

It has been unexpectedly found that CHX and STPP can be formulated in such a way to prevent precipitation (or to re-dissolve the precipitate) through the inclusion of the mild, cationic surfactant cetylpyridinium chloride (CPC).

For the following experiments, a 0.2 wt. % aqueous solution of chlorhexidine gluconate is prepared according to Table 4 below, but with a "hole" for 1.6% STPP and 0-1.0% surfactant/water. Five formulations are prepared which vary only in the amounts of water and CPC surfactant. For each formulation, the appropriate amount of CPC and/or water is added to the initial stock solution, followed by stirring for 30 minutes. The STPP is then added, followed by stirring for an additional 30 minutes. Citric acid (0.20 g) is then added to adjust the pH to 6-6.10.

TABLE 4

| Formulation | CHX (Wt. %) | CPC (Wt. %) | STPP (Wt. %) | pH | Visual |
|---|---|---|---|---|---|
| 4-1 | 0.20% | 0.00% | 1.60% | 6.08 | Clear solution with significant precipitated solid |
| 4-2 | 0.20% | 0.25% | 1.60% | 6.05 | Very opaque solution, no solid |
| 4-3 | 0.20% | 0.50% | 1.60% | 6.03 | Clear, colorless solution |
| 4-4 | 0.20% | 0.75% | 1.60% | 6.07 | Clear, colorless solution |
| 4-5 | 0.20% | 1.00% | 1.60% | 6.01 | Clear, colorless solution |

Precipitation occurs upon addition of STPP in all samples. It is noteworthy that the precipitate in the control sample (i.e., no CPC added) exhibited a solid white appearance with distinct particles whereas the samples containing CPC appeared as a hazy solution (with the exception of 0.25% CPC sample where some solid white particles were observed). The initial pH of each solution prior to pH adjustment is from 9.50 to 9.56. After subsequent pH adjustment to 6.00±0.10, the samples comprising 0.50-1.00% CPC dissolved and remained a clear solution (FIG. 1). Without being bound by theory, it is believed that the initial precipitation in the samples comprising 0.50-1.00% CPC occurs due to an increase in pH with concomitant formation of neutral CHX which is insoluble in water. However, in the control it is believed that an insoluble complex is formed between CHX and STPP which does not dissolve upon acidification. Other cationic surfactants (e.g., benzalkonium chloride) were evaluated as well, however a stabilization effect was not observed for these other cationic surfactants.

The invention claimed is:

1. An oral care composition comprising
   (i) chlorhexidine in an amount of 0.1 to 0.5 wt. %;
   (ii) sodium tripolyphosphate in an amount of 0.5 wt. % to 2 wt. %; and
   (iii) a stabilizing amount of a zwitterionic, cationic, or nonionic surfactant, or a fatty acyl amide or fatty acyl ester carboxylate or sulfonate surfactant, or a combination thereof;
   wherein the surfactant is selected from:
      (a) 0.32 to 0.33 wt. % of cocamidopropyl betaine (CAPB); or
      (b) 0.5 to 1.0 wt. % cetylpyridinium chloride (CPC); or
      (c) 0.98 to 1.1 wt. % of alkyl polyglucoside (APG); or
      (d) 0.3 to 0.5% sodium methyl cocoyl taurate;
      based on the total weight of the composition.

2. The composition of claim 1, wherein the chlorhexidine is in the form of chlorhexidine digluconate.

3. The composition of claim 1, wherein the composition comprises from 0.1 to 0.3 wt. % of the chlorhexidine, based on the total weight of the composition.

4. The composition of claim 1, wherein the composition further comprises tetrasodium pyrophosphate, tetrapotassium pyrophosphate, or combinations thereof.

5. The composition of claim 1, wherein the composition comprises:
   (i) chlorhexidine in an amount of 0.2 wt. %;
   (ii) sodium tripolyphosphate in an amount of 1.6 wt. %; and
   (iii) a surfactant and pH selected from:
      (a) 0.32 to 0.33 wt. % of cocamidopropyl betaine (CAPB) and a pH of 6.1-6.2; or
      (b) 0.5 to 1.0 wt. % cetylpyridinium chloride (CPC) and a pH of 6-6.1; or
      (c) 0.98 to 1.1 wt. % of decyl glucoside and a pH of 5.5-7; or
      (d) 0.3 to 0.5% sodium methyl cocoyl taurate and a pH of 5-8;
      the concentration ranges based on the total weight of the composition.

6. The composition of claim 1, wherein the sodium tripolyphosphate is present in an amount of 1.0 wt. % to 2 wt. %, based on the total weight of the composition.

7. The composition of claim 1, wherein the surfactant is 0.32 to 0.33 wt. % cocamidopropyl betaine (CAPB).

8. The composition of claim 1, wherein the surfactant is 0.5 to 1.0 wt. % cetylpyridinium chloride (CPC).

9. The composition of claim 1, wherein the surfactant is 0.98 to 1.1 wt. % of alkyl polyglucosides.

10. The composition of claim 9, wherein the alkyl polyglucoside is a C8-C20 glucoside.

11. The composition of claim 10, wherein the surfactant is decyl glucoside.

12. The composition of claim 1, wherein the surfactant is 0.3 to 0.5 wt. % of sodium methyl cocoyl taurate.

13. The composition of claim 1, wherein the composition comprises 70% to 95% water, based on the total weight of the composition.

14. The composition of claim 1, wherein the composition has a pH of 4 to 9.

15. The composition of claim 1, wherein the composition comprises one or more of a thickener, a buffer, a humectant, an abrasive, a sweetener, a flavorant, a pigment, a dye, an anti-caries agent, a fluoride source, an anti-bacterial agent, a whitening agent, a desensitizing agent, a preservative, an amino acid, or a mixture thereof.

16. The composition of claim 1, wherein the composition is a mouthwash.

17. A method for
   a) the treatment and/or inhibition of a chemical stain, plaque, and/or tartar on a dental surface,
   b) the treatment and/or inhibition of gum disease,
   c) the treatment and/or inhibition of halitosis,
   d) inhibiting biofilm formation on a dental surface, and/or
   e) treating and/or inhibiting bacteria from aggregating and forming bigger colonies in an oral cavity
   comprising contacting a dental surface with a composition according to claim 1.

18. The composition of claim 1, wherein the composition comprises from 0.1 to 0.3 wt. % of chlorhexidine and from 1.0 wt. % to 2 wt. % of sodium tripolyphosphate, based on the total weight of the composition.

19. The composition of claim 1, wherein the composition comprises 0.2 wt. % of the chlorhexidine and 1.6 wt. % sodium tripolyphosphate, based on the total weight of the composition.

* * * * *